(12) United States Patent
Dhanoa et al.

(10) Patent No.: US 6,586,453 B2
(45) Date of Patent: Jul. 1, 2003

(54) SUBSTITUTED THIAZOLES AND THE USE THEREOF AS INHIBITORS OF PLASMINOGEN ACTIVATOR INHIBITOR-1

(75) Inventors: Dale S. Dhanoa, Laguna Niguel, CA (US); Declan E. Ryan, West Chester, PA (US); Ingrid Deckman, Berwyn, PA (US); Anthony Sapienza, West Chester, PA (US)

(73) Assignee: 3-Dimensional Pharmaceuticals, Inc., Exton, PA (US)

( * ) Notice: Subject to any disclaimer, the term of this patent is extended or adjusted under 35 U.S.C. 154(b) by 0 days.

(21) Appl. No.: 09/822,351

(22) Filed: Apr. 2, 2001

(65) Prior Publication Data

US 2001/0044545 A1 Nov. 22, 2001

Related U.S. Application Data

(60) Provisional application No. 60/194,505, filed on Apr. 3, 2000.

(51) Int. Cl.$^7$ .............................................. A61K 31/425
(52) U.S. Cl. ....................................... 514/365; 514/369
(58) Field of Search ................................. 514/365, 369

(56) References Cited

U.S. PATENT DOCUMENTS

| | | | |
|---|---|---|---|
| 3,192,225 A | 6/1965 | Spivack et al. | 260/306.8 |
| 3,299,087 A | 1/1967 | Spivack et al. | 260/306.8 |
| 3,467,666 A | 9/1969 | Dexter et al. | 260/306.8 |
| 4,001,420 A | * 1/1977 | Malen et al. | |
| 4,942,242 A | 7/1990 | Kojima et al. | 548/192 |
| 5,217,971 A | * 6/1993 | Takasugi et al. | |
| 5,298,515 A | 3/1994 | Schubert et al. | 514/361 |
| 5,342,851 A | 8/1994 | Sanfilippo et al. | 514/370 |
| 5,530,000 A | 6/1996 | Sanfilippo et al. | 514/252 |
| 5,665,724 A | 9/1997 | Sanfilippo et al. | 514/256 |
| 5,731,328 A | 3/1998 | Berg et al. | 514/324 |
| 5,792,798 A | 8/1998 | Berg et al. | 514/648 |

FOREIGN PATENT DOCUMENTS

WO    WO 93/19054    9/1993

OTHER PUBLICATIONS

Behera, G.B. et al., "Quaternization of Thiazoles," *J. Org. Chem.* 38:2164–2166, American Chemical Society (1973).

Joshi, K.C. and Giri, S. "Organic Pesticides. Part IX. Synthesis of some 2–Arylamino–4–substituted Phenylthiazoles and their Acetoxy–mercuri Derivatives," *Jour. Indian Chem. Soc.* 39:18–19, Indian Chemical Society (1962).

Joshi, K.C. et al., "Synthesis of Some New Fluorine Containing 2–(N–Arylamino)/2–methyl–4–aryl Thiazoles and Their Bacterial Activity," *Agric. Biol. Chem.* 43:199–201, Nippon Nogei Kagakkai (1979).

Khadse, B.G. et al., "Synthesis of 4–Aryl–& 4–Heteroaryl–2–(substituted–phenylamino)thiazoles as Antitubercular Agents," *Ind. J. Chem.* 20B:683–685, Council of Scientific & Industrial Research (1981).

Khan, R.H. and Bahel, S.C., "Synthesis of Fluoroarylthiazoles and Related Compounds as Possible Fungicides," *Agr. Biol. Chem.* 40:1129–1135, Nippon Nogei Kagakkai (1976).

Mahapatra, G.N. and Rout, M.K., "Preparation of N–Substituted 2–Aminothiazoles. Part 1. Condensation of Acetophenone with Substituted Thioureas," *Jour. Indian Chem. Soc.* 30:398–400, Indian Chemical Society (1953).

Modi, J.D. et al., "Potential Anticancer Agents. Nitrogen Mustards of Aminophenylthiazoles," *J. Med. Chem.* 14:887–888, American Chemical Society (1971).

Olin, J.F. and Johnson, T.B., "Synthesis of 4–Phenylthiazole–2–Methanol and Some of its Derivatives. VIII.," *J. Amer. Chem. Soc.* 53:1471–1472, American Chemical Society (1931).

Reddy–Sastry, C.V. et al., "Synthesis & Biological Activity of Some New 6–Isothiocyanato–, 6–N–[N,N–Bis(methoxycarbonyl)guanidino]–, & 6–(Aryl/2–arylaminothiazol–4–yl)–2H–1, 4–benzoxazin–3(4H)–ones," *Ind. J. Chem.* 26B: 662–665, Council of Scientific & Industrial Research (1987).

Rinde, S.S. et al., "Synthesis of Some Thiazole Substituted Phenylamino–4–thiazolidinones," *J. Ind. Chem. Soc.* 62:334–335, Indian Chemical Society (1985).

(List continued on next page.)

Primary Examiner—Sreeni Padmanabhan
Assistant Examiner—San-ming Hui
(74) Attorney, Agent, or Firm—Sterne, Kessler, Goldstein & Fox, P.L.L.C.

(57) ABSTRACT

The present invention relates to the use of aminothiazole derivatives of Formula I of as inhibitors of PAI-1, and to novel classes of aminothiazole derivatives, their synthesis and their use as inhibitors of PAI-1. It has been discovered that compounds of Formula I:

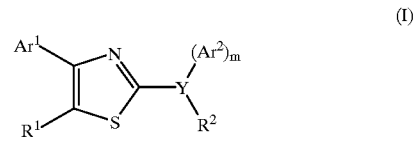

(I)

or a solvate, hydrate or a pharmaceutically acceptable salt thereof, wherein

Y, $Ar^1$, $Ar^2$, $R^1$, $R^2$, Z, m and n are described in the specification, inhibit plasminogen activator inhibitor-1 (PAI-1). These compounds can be used in the prophylaxis or for the treatment of thrombosis, angina pectoris, cerebral infarction, myocardial infarction, pulmonary infarction, intra-atrial thrombus in atrial fibrillation, deep venous thrombus, disseminated intravascular coagulation syndrome, diabetic complications, restenosis and stroke.

11 Claims, No Drawings

OTHER PUBLICATIONS

Sabnis, S.S., "Synthesis of Potential Anticancer Agents Derived from Benzaldehyde Nitrogen Mustard & Aminophenylthiazoles," *Ind. J. Chem.* 5:619–621, Council of Scientific & Industrial Research (1967).

Seligman, R.B. et al., "Some Derivatives of p–Aminosalicyclic Acid," *J. Amer. Chem. Soc.* 75:6334–6335, American Chemical Society (1953).

Sharma, G.M. et al., "Thiopegan Derivatives–XXI. A Mechanism for the Formation of 9:10 and 10:11 Thiopegan Derivatives," *Tetrahedron* 15:53–59, Pergamon Press Ltd. (1961).

Shingare, M.S. and Ingle, D.B., "Synthesis of Some Sulfonamide Derivatives," *J. Ind. Chem. Soc.* 54:705–708, Indian Chemical Society (1977).

Singh, J.M., "Studies of the chemistry of azole derivatives. IV. New N–substituted 2–aminothiazoles," *Can. J. Chem.* 46:1168–1169, NRC Research Press (1968).

International Search Report for International Application No. PCT/US01/10307.

Joshi, K.C. et al., "Synthesis of Some New Fluorine Containing 2–(N–Arylamino)/2–methyl–4–aryl Thiazoles and Their Bacterial Activity," *Agric. Biol. Chem.* 43:199–201, Agricultural Chemical Society of Japan (1979).

Khan, R.H. and Bahel, S.C., "Synthesis of Fluoroarylthiazoles and Related Compunds as Possible Fungicides," *Agr. Biol. Chem.* 40:1129–1135, Agricultural Chemical Society of Japan (1976).

Manian, A.K. et al., "Synthesis of 2–Substituted–Anilino/ Phenyl/ Benzyl–5–Substituted–4–Phenylamido–(3–o–Chlorophenyl–5–Methylisoxazolyl) Thiazoles as Potential Antitubercular and Antimicrobial Agents," *Indian Drugs* 31:442–444, Indian Drug Manufacturers' Association (1994).

Metri, J. et al., "Synthesis of New Sulphamylanilino Substituted Thiazoles of Potential Biological Activity," *Egypt. J. Chem.* 25:187–189, National Information and Documentation Centre, NIDOC Dokki (1982).

Nath, J.P. et al., "Synthesis & Halogenation of Some New 2–(o–Mercaptophenyl) amino–4–substituted–thiazoles & Oxazoles as Pesticides," *Indian J. Chem.* 18B:384–386, Council of Scientific and Industrial Research (1979).

Panigrahi, A.K. et al., "Arsenic Derivatives of Thiazoles," *J. Inst. Chemists (India)* 42:17–21, Organon (India) Ltd. (1970).

Pathak, R.B. et al., "Synthesis of Some Fluoroarylthiazoles and Related Compounds as Potential Fungicides," *J. Antibact. Antifung. Agents* 9: 477–480, Research Society for Antibacterial and Antifungal Agents, Japan (1981).

Pathak, V.N. and Singh, R.P., "Synthesis and Biological Activities of Some New 2–(N–Arylamino)–4–(Fluoroaryl) thiazoles," *J. Indian Chem. Soc.* 56:1010–1012, Indian Chemical Society (1979).

Patil, V.H. and Ingle, D.B., "2–Aryl amino–4–'4'(benzene sulphonamido)–phenyl–thiazoles," *J. Indian Chem. Soc.* 59:1000–1003, Indian Chemical Society (1982).

Rindhe, S.S. et al., "Synthesis of Some Thiazole Substituted Phenylimino–4–thiazolidinones," *J. Indian Chem. Soc.* 62:334–335, Indian Chemical Society (1985).

Sawhney, S.N. et al., "Synthesis and Anti–inflammatory Activity of 2–Amino– & 2–Alkylamino–6–benzothiazoleacetic Acids, 4–(2'–Benzothiazolylamino)–, 4–(4'–Substituted–2–thiazolylamino)–& 4–(4'–Substituted–3–alkyl–$\Delta^{4'}$thiazoline–2'–(imino)–phenylacetic Acids," *Indian J. Chem.* 16B:605–609, Council of Scientific and Industrial Research (1978).

Singh, H. et al., "Thiopegan Derivatives: Part XXXIV— Reactions of Ethyl Anthranilate Thiocyanate," *Indian. J. Chem.* 7:571–574, Council of Scientific and Industrial Research (1969).

Singh, S.P. et al., "TLC Separation of Some Isomeric 2– and 6–[2–Amino (and substituted amino)–4–thiazolyl] Benzothiazoles," *Fres. Z. Anal. Chem.* 288:285, Springer–Verlag (1977).

Singl, S.P. et al., "Studies in Hantzsch thiazole synthesis: Part 2—Reactions of thiocarboxamides with α–haloketones," *Indian J. Chem.* 29B:533–538, Publications and Information Directorate, CSIR (1990).

Thakar, K.A. et al., "Synthesis of 2–(Substituted Anilino) 4–(Substituted Phenyl) thiazoles," *J. Pharm. Sci.* 67:587–589, American Pharmaceutical Association (1978).

STN Easy Abstract for Document AT11, Accession No. 1984:630402 CAPLUS, <<http://stneasy.cas.org/tmp/ 27038–1842628305–200/727859240.html>>.

Bajou, K., et al., "Absence of host plasminogen activator inhibitor 1 prevents cancer invasion and vascularization," *Nat. Med.* 4:923–928, Nature America (1998).

Björquist, P., et al., "Identification of the Binding Site for a Low–Molecular–Weight Inhibitor of Plasminogen Activator Inhibitor Type 1 by Site–Directed Mutagenesis," *Biochem.* 37:1227–1234, American Chemical Society (1998).

Charlton, P., et al., "XR5118, a novel modulator of plasminogen activator inhibitor–1 (PAI–1), increases endogenous tPA activity in the rat," *Fibrinol. Proteol.* 11:51–56, Pearson Professional Ltd. (1997).

Charlton, P.A., et al., "Evaluation of a Low Molecular Weight Modulator of Human Plasminogen Activator Inhibitor–1 Activity," *Thromb. Haemo.* 75:808–815, Schattauer GmbH (1996).

Friederich, P.W., et al., "Novel Low–Molecular–Weight Inhibitor of PAI–1 (XR5118) Promotes Endogenous Fibrinolysis and Reduces Postthrombolysis Thrombus Growth in Rabbits," *Circ.* 96:916–921, American Heart Association, Inc. (1997).

Kluft, C., et al., "The postoperative fibrinolytic shutdown: a rapidly reverting acute phase pattern for the fast–acting inhibitor of tissue–type plasminogen activator after trauma," *Scand. J. Clin. Lab. Invest.* 45:605–610, Blackwell Scientific Publisher (1985).

Kruithof, E.K.O., et al., "Plasminogen Activator Inhibitor 1: Development of a Radioimmunoassay and Observations on Its Plasma Concentration During Venous Occlusion and After Platelet Aggregation," *Blood* 70:1645–1653, Grune and Stratton, Inc. (1987).

Lawrence, D.A., et al., "Localization of Vitronectin Binding Domain in Plasminogen Activator Inhibitor–1," *J. Biol. Chem.* 269:15223–15228, American Society for Biochemistry and Molecular Biology, Inc.(1994).

Liu, G., et al., "Co–expression of Urokinase, Urokinase Receptor and PAI–1 is Necessary for Optimum Invasiveness of Cultured Lung Cancer Cells," *Int. J. Cancer* 60:501–506, Wiley–Liss, Inc. (1995).

Lundgren, C.H., et al., "Elaboration of Type–1 Plasminogen Activator Inhibitor From Adipocytes: A Potential Pathogenetic Link between Obesity and Cardiovascular Disease," *Circ.* 93:106–110, American Heart Association, Inc. (1996).

Lupu, F., et al., "Localization and Production of Plasminogen Activator Inhibitor–1 in Human Healthy and Atherosclerotic Arteries," *Arterio. Thromb.* 13:1090–1100, American Heart Association, Inc. (1993).

Padró, T., et al., "Quantification of Plasminogen Activators and Their Inhibitors in Aortic Vessel Wall in Relation to the Presence and Severity of Atherosclerotic Disease," *Arterio. Thromb. Vasc. Biol.* 15:893–902, American Heart Association, Inc. (1995).

Patrassi, G.M., et al., "Familial Thrombophila Associated with High Levels of Plasminogen Activator Inhibitor," *Fibrinolysis* 6:99–103, Longman Group U.K. Ltd. (1992).

Sawa, H., et al., "Potentiation by Hypercholesterolemia of the Induction of Aortic Intramural Synthesis of Plasminogen Activator Inhibitor Type 1 by Endothelial Injury," *Circ. Res.* 73:671–680, American Heart Association, Inc. (1993).

Sobel, B. E. et al., "Increased Plasminogen Activator Inhibitor Type 1 in Coronary Artery Atherectomy Specimnes From Type 2 Diabetic Compared With Nondiabetic Patients: A Potential Factor Predisposing to Thrombosis and Its Persistence," *Circ.* 97:2213–2221, American Heart Association, Inc. (1998).

Tsuchiya, H., et al., "The Antibody to Plasminogen Activator Inhibitor–1 Suppresses Pulmonary Metastases of Human Fibrosarcoma in Athymic Mice," *Gen. Diag. Pathol.* 141:41–48, Gustav Fischer (1995).

Dialog File 351, Accession No. 2567225, Derwent WPI English language abstract for JP 55133366 (Document AL1).

Dialog File 351, Accession No. 7183583, Derwent WPI English language abstract for JP 62108859 A2 (Document AM1).

Dialog file 351, Accession No. 7268328, Derwent WPI English language abstract for EP 0 237 929 B1 (Document AN1).

Dialog file 351, Accession No. 9802848, Derwent WPI English language abstract for WO 94/01423 (Document AP1).

* cited by examiner

SUBSTITUTED THIAZOLES AND THE USE THEREOF AS INHIBITORS OF PLASMINOGEN ACTIVATOR INHIBITOR-1

This application claims the priority benefit under 35 U.S.C. § 119 of U.S. Provisional Appl. No. 60/194,505, filed Apr. 3, 2000, the entirety of which is incorporated by reference herein.

BACKGROUND OF THE INVENTION

1. Field of the Invention

The present invention is in the field of inhibitors of plasminogen activator inhibitor-1 (PAI-1) activity. More particularly, the invention relates to the use of substituted thiazoles as inhibitors of PAI-1, and to novel classes of 2-substituted thiazole derivatives, their synthesis and their use as inhibitors of PAI-1.

2. Related Art

PAI-1 is a naturally occurring serine protease inhibitor, or serpin, that rapidly inhibits the activity of several proteases, including tissue plasminogen activator (tPA) and urokinase plasminogen activator (uPA), by forming equimolar, irreversible complexes that are internalized and degraded. In this capacity, PAI-1 plays a major role in preventing fibrinolysis by decreasing the level of tPA and/or uPA, and consequently, the level of plasminogen converted to plasmin. Plasmin is an enzyme critical to the lysis of fibrin clots and works by cleaving fibrin to small soluble products.

PAI-1 can contribute to a variety of coronary diseases by retarding the clearance of thrombi. Elevated levels of PAI-1 have been described to correlate with an increased risk of atherosclerosis (Lupu, F., et al., Arteriosclerosis and Thrombosis 13:1090–1100 (1993)), deep vein thrombosis (Patrassi, G. M., et al., Fibrinolysis 6:99–102 (1992)) and of thrombosis during sepsis, surgery and trauma (Kluft, C., et al., Scand. J. Clin. Lab. Invest. 45:605–610 (1985)). Elevated PAI-1 levels are also thought to contribute to the high incidence of coronary disease in individuals with Type 2 diabetes (Sobel, B. E., et al., Circulation 97(22):2213–2221 (1998)), obese individuals (Lundgren, C. H., et al., Circulation 93(1):106–110 (1996)), and the elderly (Lupu, F., et al., Arteriosclerosis and Thrombosis 13:1090–1100 (1993)).

Increased PAI-1 has been demonstrated in human atherosclerotic vessel walls and may contribute to the impaired plasma fibrinolytic capacity in patients at high risk of atherothrombotic events. The atherosclerotic process begins with an injury to the inner lining of the blood vessel, the endothelium. Smooth muscle cells migrate from their normal location in the media to the intima, where they divide and make up a bulk lesion.

Immunohistochemical analyses have revealed that most of the PAI-1 in the thickened intima of early lesions is located in and around neointimal smooth muscle cells and possibly macrophages. Both of these cell types can become lipid-laden foam cells that form fatty streaks, another hallmark feature of atherosclerosis.

In advanced lesions, larger amounts of PAI-1 are expressed by smooth muscle cells and macrophages in the necrotic core. Most of the PAI-1 of this advanced stage is in complex tPA, suggesting that PAI-1 has an important function in modulating mural tPA activity (Padro, T., et al., Arterioscler. Thromb. Vasc. Biol. 15:893–902 (1995) and Saweh, H., et al., Circ. Res. 73:671–680 (1993)). These findings have been supported with experimental work in rabbits that demonstrated an increase in PAI-1 expression in activated endothelial cells, macrophages and smooth muscle cells in response to sustained mechanical injury. The increase in PAI-1 transcription paralleled the severity of vascular lesions induced and was increased in hypercholesterolemic rabbits (Kruithof, E. K. O., et al., Blood 70:1645–1653 (1987)). These results suggest that enhanced PAI-1 expression is a feature of early atherosclerosis and that a PAI-1 inhibitor may be effective preventive therapeutics for high risk patients.

A PAI-1 inhibitor may also serve as an anticancer agent. An antibody to PAI-1 has been shown to suppress metastasis in several cancer models (Tsuchiya, H., et al., Gen. Diag., Pathol. 141:41–48 (1995)). In cultured lung cancer cells, PAI-1 is necessary for optimum invasion (Liu, G., et al., Int. J. Cancer 60:501–506 (1995)). Further, cancer invasion and tumor vascularization have been prevented in PAI-1 knockout mice implanted with malignant murine keratinocytes (Bajou, K., et al., Nature Med. 4(8):923–928 (1998)). This indicates that PAI-1 plays an integral role in tumor progression.

PAI-1 is also expressed at high levels by smooth muscle and endothelial cells, and it regulates the proteolytic activity surrounding the formation of blood vessels. A PAI-1 inhibitor may be suitable as an anti-angiogenic agent by hindering proper vessel formation around tumor. In fact, transduced endothelial cells that express decreased PAI-1 activity compared with normal endothelial cells were found to form large ectactic sac-like structures resembling haemangiomas when cultured in fibrin gels, suggesting abnormal vessel formation (Lawrence, D. A., et al., J. Biol. Chem. 269(21):15223–15229 (1994)).

U.S. Pat. No. 4,942,242 discloses compounds of the following Formula:

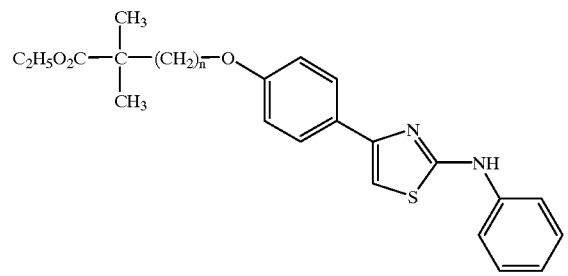

wherein n is 3 or 4. These compounds are disclosed to be useful as inhibitors of blood platelet aggregation.

JP 61016274 describes, for example, the following thiazole derivatives that are stated to have platelet aggregation inhibitory activity:

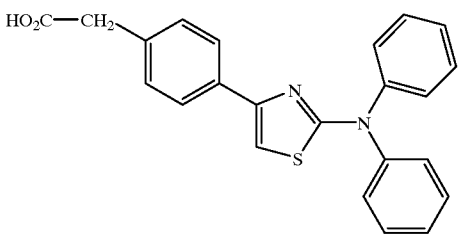

-continued

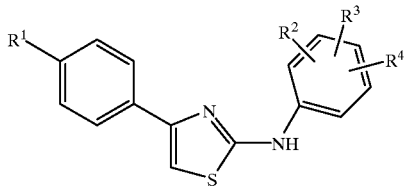

wherein $R^1$ is $CH_2COOH$ or $CHMeCOOH$ and $R^2$, $R^3$ and $R^4$ are independently selected from the group consisting of H, $CH_3$, $OCH_3$ and Cl, and

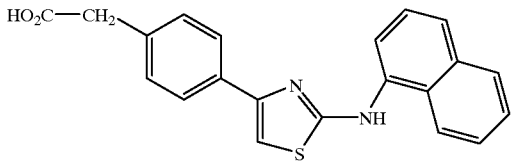

A need exists in the art for compounds that are potent and/or selective inhibitors of PAI-1.

SUMMARY OF THE INVENTION

It has now been discovered that thiazole derivatives of Formula I:

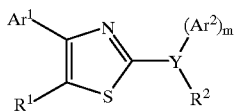

(I)

or a solvate, hydrate or a pharmaceutically acceptable salt thereof, wherein

Y is —N—, —C($R^3$)— or —CH($R^3$)—, wherein $R^3$ is selected from the group consisting of hydrogen, cyano, $C(CN)_3$, $N(CN)_2$, trifluoromethyl, halogen, alkyl, cycloalkyl, aryl and heteroaryl radical, all of which can be optionally substituted;

$Ar^1$ and $Ar^2$, which can be the same or different, are an optionally substituted aryl or an optionally substituted heteroaryl radical;

m is 0 or 1, provided that when Y is —N— or —C($R^3$)—, then m is 1, and when Y is —CH($R^3$)—, then m is 0;

$R^1$ is selected from the group consisting of hydrogen, alkyl, cycloalkyl, and aryl or heteroaryl radical, all of which can be optionally substituted; and $R^2$ is hydrogen, or an optionally substituted aryl or an optionally substituted heteroaryl radical; with the provisos that when Y is N, $R^1$ and $R^2$ are hydrogen and $Ar^2$ is an optionally substituted phenyl, then $Ar^1$ is other than a phenyl group substituted with carboxyalkyl or an alkyl ester of carboxyalkyloxy;

when Y is N, $R^1$ is hydrogen, and $Ar^2$ and $R^2$ are both a phenyl group, then $Ar^1$ is other than a phenyl group substituted with carboxyalkyl; or when Y is N, $R^1$ and $R^2$ are hydrogen and $Ar^2$ is naphthyl, then $Ar^1$ is other than a phenyl group substituted with carboxyalkyl, inhibit plasminogen activator inhibitor-1 (PAI-1). These compounds can be used in the prophylaxis or for the treatment of thrombosis, angina pectoris, cerebral infarction, myocardial infarction, pulmonary infarction, intra-atrial thrombus in atrial fibrillation, deep venous thrombus, disseminated intravascular coagulation syndrome, diabetic complications, restenosis and stroke.

Accordingly, the present invention provides a method of inhibiting plasminogen activator inhibitor-1. The method comprises administering to a mammal in need thereof an effective amount of a compound of Formula I.

Also, the present invention provides a method for preventing or treating one or more of thrombosis, angina pectoris, cerebral infarction, myocardial infarction, pulmonary infarction, intra-atrial thrombus in atrial fibrillation, deep venous thrombus, disseminated intravascular coagulation syndrome, diabetic complications, restenosis, for example, after percutaneous transluminal coronary angioplasty, or stroke by administering to a mammal in need thereof an effective amount of a compound of Formula I.

A number of compounds useful in the present invention have not been heretofor reported. Thus, the present invention also provides novel thiazole derivatives included in Formula I. Also, the present invention provides a method for preparing the novel compounds included in Formula I.

Further, the present invention provides pharmaceutical and veterinary compositions for inhibiting plasminogen activator inhibitor-1, comprising an effective amount of one or more of the compounds of Formula I–VI in a mixture with one or more pharmaceutically acceptable carriers or diluents.

Additional embodiments and advantages of the invention will be set forth in part in the description as follows, and in part will be obvious from the description, or may be learned by practice of the invention. The embodiments and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

DETAILED DESCRIPTION OF THE PREFERRED EMBODIMENTS

Applicants have discovered that plasminogen activator inhibitor-1 can be effectively inhibited by compounds of Formula I:

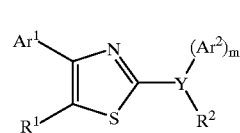

(I)

or a solvate, hydrate or a pharmaceutically acceptable salt thereof, wherein

Y is —N—, —C($R^3$)— or —CH($R^3$)—, wherein $R^3$ is selected from the group consisting of hydrogen, cyano, $C(CN)_3$, $N(CN)_2$, trifluoromethyl, halogen, alkyl, cycloalkyl, aryl and heteroaryl radical, all of which can be optionally substituted;

$Ar^1$ and $Ar^2$, which can be the same or different, are an optionally substituted aryl or an optionally substituted heteroaryl;

m is 0 or 1, provided that when Y is —N— or —C(R³)—, then m is 1, and when Y is —CH(R³)—, then m is 0;

R¹ is selected from the group consisting of hydrogen, alkyl, cycloalkyl, and aryl or heteroaryl radical, all of which can be optionally substituted; and R² is hydrogen, or an optionally substituted aryl or an optionally substituted heteroaryl radical;

with the provisos that when Y is N, R¹ and R² are hydrogen and Ar² is an optionally substituted phenyl, then Ar¹ is other than a phenyl group substituted with carboxyalkyl or an alkyl ester of carboxyalkyloxy;

when Y is N, R¹ is hydrogen, and Ar² and R² are both a phenyl group, then Ar¹ is other than a phenyl group substituted with carboxyalkyl; or when Y is N, R¹ and R² are hydrogen and Ar² is naphthyl, then Ar¹ is other than a phenyl group substituted with carboxyalkyl.

Therefore, these compounds can be used in the prophylaxis or for the treatment of thrombosis, angina pectoris, cerebral infarction, myocardial infarction, pulmonary infarction, intra-atrial thrombus in atrial fibrillation, deep venous thrombus, disseminated intravascular coagulation syndrome, diabetic complications, restenosis, for example, after percutaneous transluminal coronary angioplasty, and stroke.

Preferred compounds falling within the scope of Formula I include compounds wherein Ar¹ and Ar² are independently selected from the group consisting of phenyl, biphenyl, naphthyl, tetrahydronaphthyl, thienyl, benzothienyl, furyl, benzofuryl, thiazolyl, imidazolyl, isoxazolyl, pyrrolyl and pyrazolyl, any of which can be optionally substituted. More preferably, Ar¹ is selected from the group consisting of phenyl, naphthyl, tetrahydronaphthyl, biphenyl and isoxazolyl and Ar² is phenyl. Especially, Ar¹ is selected from the group consisting of tetrahydronaphthyl, biphenyl and isoxazolyl.

The aryl and heteroaryl groups are preferably optionally substituted by one or more substituents independently selected from the group consisting of alkyl, halogen, haloalkyl, hydroxy, hydroxyalkyl, amino, aminoalkyl, alkoxy, alkoxyalkyl, nitro, cyano, thiol, alkylthiol, acylamino, acyloxy, carboxy, carboxyalkyl, —C(O)O-alkyl, —C(O)NH-alkyl, —NHR⁴, —NR⁴R⁵, phenoxy, and benzyloxy, wherein R⁴ and R⁵ are selected from the group consisting of alkyl, —C(O)O-alkyl, aroyl, —C(O)NH-alkyl, —O—C(O)-alkyl and —C(O)NH-aryl. More preferably, the optional substituents are selected from the group consisting of $C_{1-6}$ alkyl, fluoro, chloro, bromo, trifluoro($C_{1-6}$)alkyl, hydroxy, hydroxy($C_{1-6}$)alkyl, amino, amino($C_{1-6}$)alkyl, $C_{1-6}$ alkoxy, nitro, cyano, carboxy, —C(O)($C_{1-6}$)alkyl, benzyloxy, $C_{1-6}$ alkylamino, di($C_{1-6}$)alkylamino, —C(O)O ($C_{1-6}$)alkyl, —O—C(O)($C_{1-6}$)alkyl and —C(O)NH($C_{1-6}$) alkyl.

Preferably, R¹ is selected from the group consisting of H, $C_{1-6}$ alkyl, $C_{3-7}$ cycloalkyl and phenyl substituted with trifluoro($C_{1-6}$)alkyl, nitro, hydroxy, $C_{1-4}$ alkyl, halogen, amino, —NHR⁴, wherein R⁴ is selected from the group consisting of $C_{1-6}$ alkyl, —C(O)($C_{1-6}$)alkyl, aroyl, —C(O)NH($C_{1-3}$)alkyl and —C(O)NH-aryl.

Preferably, R² is selected from the group consisting of hydrogen and a phenyl radical optionally substituted by trifluoro($C_{1-6}$)alkyl, nitro, hydroxy, $C_{1-6}$ alkoxy, halogen, amino, cyano, $C_{1-6}$ alkyl and —NHR⁴, wherein R⁴ is selected from the group consisting of $C_{1-6}$ alkyl, —C(O) ($C_{1-6}$)alkyl, aroyl, —C(O)NH—($C_{1-3}$) alkyl and —C(O) NH-aryl.

Preferably, R¹ and R² are both hydrogen in Formula I.

One group of useful compounds of the invention are compounds of Formula II:

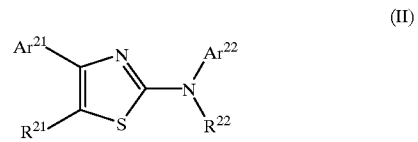

(II)

or a solvate, hydrate or a pharmaceutically acceptable salt thereof, wherein

Ar²¹ is an optionally substituted aryl or an optionally substituted heteroaryl radical;

Ar²² is a substituted aryl or an optionally substituted heteroaryl radical;

R²¹ is selected from the group consisting of hydrogen, alkyl, cycloalkyl, and aryl or heteroaryl radical, all of which can be optionally substituted;

R²² is hydrogen or an optionally substituted aryl or an optionally substituted heteroaryl radical, with the provisos that when R²¹ and R²² are hydrogen and Ar²² is substituted phenyl, then Ar²¹ is other than a phenyl group substituted with carboxyalkyl;

when R²¹ is hydrogen, and Ar²² and R²² are both a phenyl group, then Ar²¹ is other than a phenyl group substituted with carboxyalkyl; or when R²¹ and R²² are hydrogen and Ar²² is naphthyl, then Ar²¹ is other than a phenyl group substituted with carboxyalkyl.

Preferably, the aryl radical is selected from the group consisting of phenyl, biphenyl, naphthyl and tetrahydronapthyl. The heteroaryl radical is preferably isoxazolyl.

Preferably, Ar²² is a phenyl group substituted with one or more of alkyl, halogen, haloalkyl, hydroxy, hydroxyalkyl, amino, aminoalkyl, alkoxy, alkoxyalkyl, nitro, cyano, thiol, alkylthiol, acylamino, acyloxy, carboxy, carboxyalkyl, —C(O)O-alkyl, —C(O)NH-alkyl, —NHR⁴, —NR⁴R⁵, phenoxy, and benzyloxy, wherein R⁴ is selected from the group consisting of alkyl, —C(O)O-alkyl, aroyl, —C(O) NH-alkyl and —C(O)NH-aryl. More preferably, Ar²² is a phenyl group substituted with one or more of $C_{1-6}$ alkyl, fluoro, chloro, bromo, trifluoro($C_{1-6}$)alkyl, hydroxy, hydroxy($C_{1-6}$)alkyl, amino, amino($C_{1-6}$)alkyl, $C_{1-6}$ alkoxy, nitro, cyano, carboxy, —C(O)O—($C_{1-6}$)alkyl and benzyloxy.

One group of preferred compounds of Formula II are those wherein Ar²¹ is a phenyl group substituted with 3,4-difluoro, 2,4-difluoro, bromo, trifluoromethyl, 3,4-dichloro, and 2,4-dichloro.

One group of preferred compounds of Formula II are those wherein Ar²² is a phenyl group substituted with carboxy, cyano, nitro, trifluoromethyl, 3,5-dichloro, 3,4-dichloro, 2,4-dichloro, 2,4,5-trichloro, 3-chloro-4-bromo, 2,4-difluoro, 2,3,4-trifluoro, hydroxy and hydroxy($C_{1-6}$) alkyl.

Preferably, R²¹ and R²² are both hydrogen in Formula II.

Preferably, when Ar²¹ is an unsubstituted naphthyl or a naphthyl substituted with halogen, R²¹ and R²² are both hydrogen, and Ar²² is a substituted phenyl group, then the substituents in Ar²² are not selected from the group consisting of alkyl, haloalkyl, halogen, thiol, and nitro.

One group of novel and useful compounds of the invention are compounds of Formula III:

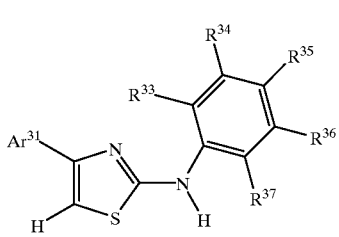

(III)

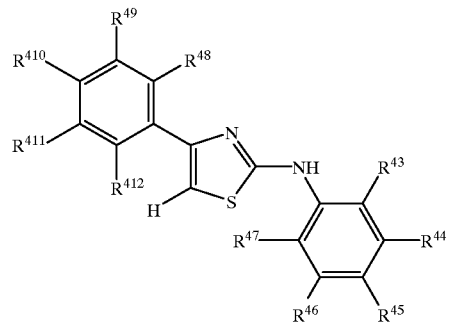

(IV)

or a solvate, hydrate or a pharmaceutically acceptable salt thereof, wherein

Ar$^{31}$ is an optionally substituted aryl or an optionally substituted heteroaryl radical selected from the group consisting of biphenyl, naphthyl, tetrahydronaphthyl and isoxazolyl; and R$^{33}$–R$^{37}$ are independently selected from the group consisting of hydrogen, alkyl, halogen, haloalkyl, hydroxy, hydroxyalkyl, amino, aminoalkyl, alkoxy, alkoxyalkyl, nitro, cyano, thiol, alkylthiol, acylamino, acyloxy, carboxy, carboxyalkyl, —C(O)O-alkyl, —C(O)NH-alkyl, —NHR$^{4}$, —NR$^{4}$R$^{5}$, phenoxy, and phenyl(C$_{1-4}$)alkyloxy, wherein R$^{4}$ is selected from the group consisting of alkyl, —C(O)O-alkyl, aroyl, —C(O)NH-alkyl and —C(O)NH-aryl, provided that at least one of R$^{33}$–R$^{37}$ is other than hydrogen, with the proviso that when Ar$^{31}$ is an unsubstituted naphthyl or a naphthyl substituted with halogen, then one or more of R$^{33}$–R$^{37}$ is not selected from the group consisting of alkyl, haloalkyl, halogen, thiol, and nitro.

Preferably, Ar$^{31}$ is optionally substituted biphenyl, tetrahydronaphthyl or isoxazolyl, more preferably optionally substituted biphenyl or tetrahydronaphthyl.

Optional substituents on Ar$^{31}$ are preferably selected from the group consisting of hydrogen, C$_{1-6}$ alkyl, halogen, hydroxy, nitro, cyano, halo(C$_{1-6}$)alkyl, hydroxy(C$_{1-6}$)alkyl, and carboxy.

When Ar$^{31}$ is tetrahydronaphthyl, it is preferably 5,5,8,8-tetramethyl-substituted or 3-ethyl-5,5,8,8-tetramethyl-substituted.

Preferably, R$^{33}$–R$^{37}$ are independently selected from the group consisting of hydrogen, C$_{1-6}$ alkyl, halogen, halo(C$_{1-6}$)alkyl, hydroxy, hydroxy(C$_{1-6}$)alkyl, amino, amino(C$_{1-6}$)alkyl, C$_{1-6}$ alkoxy, C$_{1-6}$ alkoxy(C$_{1-6}$)alkyl, nitro, cyano, thiol, C$_{1-6}$ alkylthiol, C$_{1-6}$ acylamino, C$_{1-6}$ acyloxy, carboxy, carboxy(C$_{1-6}$)alkyl, —C(O)O—C$_{1-6}$ alkyl, —C(O)NH—C$_{1-6}$ alkyl, C$_{1-6}$ alkylamino, di(C$_{1-6}$)alkylamino, phenoxy, and benzyloxy. More preferably, R$^{33}$–R$^{37}$ are independently selected from the group consisting of hydrogen, C$_{1-4}$ alkyl, halogen, halo(C$_{1-4}$)alkyl, trifluoro(C$_{1-4}$)alkyl, hydroxy, hydroxy(C$_{1-4}$)alkyl, amino, amino(C$_{1-4}$)alkyl, C$_{1-4}$ alkoxy, nitro, cyano, C$_{1-4}$ acylamino, C$_{1-4}$ acyloxy, carboxy, carboxy(C$_{1-4}$)alkyl, —C(O)O—C$_{1-4}$ alkyl, —C(O)NH—C$_{1-4}$ alkyl, C$_{1-4}$ alkylamino, di(C$_{1-4}$)alkylamino, phenoxy, and benzyloxy. Most preferably, R$^{33}$–R$^{37}$ are independently selected from the group consisting of hydrogen, fluoro, chloro, bromo, trifluoromethyl, hydroxy, hydroxymethyl, hydroxyethyl, nitro, cyano, methoxy, carboxy, and benzyloxy.

Also, one group of novel and useful compounds of the invention are compounds of Formula IV:

or a solvate, hydrate or a pharmaceutically acceptable salt thereof, wherein at least one of R$^{48}$–R$^{412}$ is trifluoro(C$_{1-6}$)alkyl and the substitutuents that are not trifluoro(C$_{1-6}$)alkyl are independently selected from the group consisting of hydrogen, C$_{1-6}$ alkyl, halogen, halo(C$_{1-6}$)alkyl, hydroxy, hydroxy(C$_{1-6}$)alkyl, amino, amino(C$_{1-6}$)alkyl, C$_{1-6}$ alkoxy, C$_{1-6}$ alkoxy(C$_{1-6}$)alkyl, nitro, cyano, thiol, C$_{1-6}$ alkylthiol, C$_{1-6}$ acylamino, C$_{1-6}$ acyloxy, carboxy, carboxy(C$_{1-6}$)alkyl, —C(O)O—C$_{1-6}$ alkyl, —C(O)NH—C$_{1-6}$ alkyl, C$_{1-6}$ alkylamino, di(C$_{1-6}$)alkylamino, phenoxy, benzyloxy, —C(O)O(C$_{1-3}$)alkyl, —O—C(O)(C$_{1-3}$)alkyl, and —NHC(O)(C$_{1-3}$)alkyl; and R$^{43}$–R$^{47}$ are independently selected from the group consisting of hydrogen, C$_{1-6}$ alkyl, halogen, halo(C$_{1-6}$)alkyl, hydroxy, hydroxy(C$_{1-6}$)alkyl, amino, amino(C$_{1-6}$)alkyl, C$_{1-6}$ alkoxy, C$_{1-6}$ alkoxy(C$_{1-6}$)alkyl, nitro, cyano, thiol, C$_{1-6}$ alkylthiol, C$_{1-6}$ acylamino, C$_{1-6}$ acyloxy, carboxy, carboxy(C$_{1-6}$)alkyl, —C(O)O-C$_{1-6}$ alkyl, —C(O)NH—C$_{1-6}$ alkyl, C$_{1-6}$ alkylamino, di(C$_{1-6}$) alkylamino, phenoxy, and benzyloxy, —C(O)O(C$_{1-3}$)alkyl, —O—C(O)(C$_{1-3}$)alkyl, and —NHC(O)(C$_{1-3}$)alkyl, provided that at least one of R$^{43}$–R$^{47}$ is other than hydrogen, with the proviso that when one of R$^{48}$–R$^{412}$ is trifluoro(C$_{1-6}$)alkyl and the other substituents are hydrogen and one of R$^{43}$–R$^{47}$ is halogen or trifluoromethyl, then at least one of R$^{43}$–R$^{47}$ that is not halogen or trifluoromethyl is other than hydrogen.

Preferred compounds of Formula IV include compounds wherein at least one of R$^{48}$–R$^{412}$ is trifluoromethyl.

Another group of novel and useful compounds of the invention are compounds of Formula IV or a solvate, hydrate or a pharmaceutically acceptable salt thereof, wherein at least one of R$^{48}$–R$^{412}$ is nitro and the substituents that are not nitro are independently selected from the group consisting of hydrogen, C$_{1-6}$ alkyl, halogen, halo(C$_{1-6}$) alkyl, hydroxy, hydroxy(C$_{1-6}$)alkyl, amino, amino(C$_{1-6}$)alkyl, C$_{1-6}$ alkoxy, C$_{1-6}$ alkoxy(C$_{1-6}$)alkyl, cyano, thiol, C$_{1-6}$ alkylthiol, C$_{1-6}$ acylamino, C$_{1-6}$ acyloxy, carboxy, carboxy(C$_{1-6}$)alkyl, —C(O)O-C$_{1-6}$ alkyl, —C(O)NH—C$_{1-6}$ alkyl, C$_{1-6}$ alkylamino, di(C$_{1-6}$)alkylamino, phenoxy, benzyloxy, —C(O)O(C$_{1-3}$)alkyl, —O—C(O)(C$_{1-3}$)alkyl, and —NHC(O)(C$_{1-3}$)alkyl; and R$^{43}$–R$^{47}$ are independently selected from the group consisting of hydrogen, C$_{1-6}$ alkyl, halogen, halo(C$_{1-6}$) alkyl, hydroxy, hydroxy(C$_{1-6}$)alkyl, amino(C$_{1-6}$)alkyl, C$_{1-6}$ alkoxy, C$_{1-6}$ alkoxy(C$_{1-6}$)alkyl, cyano, C$_{1-6}$ alkylthiol, C$_{1-6}$ acylamino, C$_{1-6}$ acyloxy, carboxy, —C(O)O—$C_{1-6}$ alkyl, —C(O)NH—$C_{1-6}$ alkyl, $C_{1-6}$ alkylamino, di($C_{1-6}$)alkylamino, phenoxy, benzyloxy, —C(O)O($C_{1-3}$)alkyl, —O—C(O)($C_{1-3}$)alkyl, and —NHC(O)($C_{1-3}$)alkyl, provided that at least one of $R^{43}$–$R^{47}$ is other than hydrogen.

Preferred compounds of Formula IV include also those, wherein at least one of $R^{48}$–$R^{412}$ is nitro and the phenyl ring is further substituted by one or more $C_{1-6}$ alkyl groups (i.e., the other of $R^{48}$–$R^{412}$ are hydrogen or $C_{1-6}$ alkyl). Preferably, $R^{49}$ and $R^{411}$ are both nitro and $R^{410}$ is a $C_{1-4}$ alkyl group, preferably t-butyl. Optionally, the phenyl ring is further substituted by two $C_{1-3}$ alkyl groups.

One group of novel and useful compounds of the invention are compounds of Formula IV or a solvate, hydrate or a pharmaceutically acceptable salt thereof, wherein at least one of $R^{43}$–$R^{47}$ is cyano and the substituents that are not cyano are independently selected from the group consisting of hydrogen, $C_{1-6}$ alkyl, halogen, halo($C_{1-6}$)alkyl, hydroxy, hydroxy($C_{1-6}$)alkyl, amino ($C_{1-6}$)alkyl, $C_{1-6}$ alkoxy, $C_{1-6}$ alkoxy($C_{1-6}$)alkyl, $C_{1-6}$ alkylthiol, $C_{1-6}$ acylamino, $C_{1-6}$ acyloxy, carboxy, —C(O)O—$C_{1-6}$ alkyl, —C(O)NH—$C_{1-6}$ alkyl, $C_{1-6}$ alkylamino, di($C_{1-6}$)alkylamino, phenoxy, benzyloxy, —C(O)O($C_{1-3}$)alkyl, —O—C(O)($C_{1-3}$)alkyl, and —NHC(O)($C_{1-3}$)alkyl; and $R^{48}$–$R^{412}$ are independently selected from the group consisting of hydrogen, $C_{1-6}$ alkyl, halogen, halo($C_{1-6}$) alkyl, hydroxy, hydroxy($C_{1-6}$)alkyl, amino, amino($C_{1-6}$)alkyl, $C_{1-6}$ alkoxy, $C_{1-6}$ alkoxy($C_{1-6}$)alkyl, nitro, cyano, thiol, $C_{1-6}$ alkylthiol, $C_{1-6}$ acylamino, $C_{1-6}$ acyloxy, carboxy, carboxy($C_{1-6}$)alkyl, —C(O)O—$C_{1-6}$ alkyl, —C(O)NH—$C_{1-6}$ alkyl, $C_{1-6}$ alkylamino, di($C_{1-6}$)alkylamino, phenoxy, benzyloxy, —C(O)O($C_{1-3}$)alkyl, —O—C(O)($C_{1-3}$)alkyl, and —NHC(O)($C_{1-3}$)alkyl.

Preferred compounds of Formula IV include also compounds wherein one or more of $R^{43}$–$R^{47}$ are hydroxy, carboxymethyl, $C_{1-4}$ alkoxy, phenoxy, benzyloxy, carboxy, —C(O)O($C_{1-3}$)alkyl or —O—C(O)($C_{1-3}$)alkyl.

One group of useful compounds of the invention are compounds of Formula V:

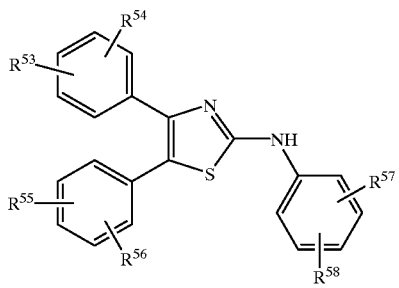

(V)

or a solvate, hydrate or a pharmaceutically acceptable salt thereof, wherein $R^{53}$–$R^{58}$ are independently selected from the group consisting of hydrogen, alkyl, halogen, haloalkyl, hydroxy, hydroxyalkyl, amino, aminoalkyl, alkoxy, alkoxyalkyl, nitro, cyano, thiol, alkylthiol, acylamino, acyloxy, carboxy, carboxyalkyl, —C(O)O-alkyl, —C(O)NH-alkyl, —NHR⁴, —NR⁴R⁵, phenoxy, and benzyloxy, wherein R⁴ is selected from the group consisting of alkyl, —C(O)O-alkyl, aroyl, —C(O)NH-alkyl and —C(O)NH-aryl.

Preferably, $R^{53}$–$R^{58}$ are independently selected from the group consisting of hydrogen, $C_{1-6}$ alkyl, halogen, halo($C_{1-6}$)alkyl, hydroxy, hydroxy($C_{1-6}$)alkyl, amino, amino ($C_{1-6}$)alkyl, $C_{1-6}$ alkoxy, $C_{1-6}$ alkoxy($C_{1-6}$)alkyl, nitro, cyano, thiol, $C_{1-6}$ alkylthiol, $C_{1-6}$ acylamino, $C_{1-6}$ acyloxy, carboxy, carboxy($C_{1-6}$)alkyl, —C(O)O—$C_{1-6}$ alkyl, —C(O)NH—$C_{1-6}$ alkyl, $C_{1-6}$ alkylamino, di($C_{1-6}$)alkylamino, phenoxy, and benzyloxy. More preferably, $R^{53}$–$R^{58}$ are independently selected from the group consisting of hydrogen, $C_{1-4}$ alkyl, halogen, halo($C_{1-4}$)alkyl, trifluoro($C_{1-4}$)alkyl, hydroxy, hydroxy($C_{1-4}$)alkyl, amino, amino($C_{1-4}$) alkyl, $C_{1-4}$ alkoxy, nitro, cyano, $C_{1-4}$ acylamino, $C_{1-4}$ acyloxy, carboxy, carboxy($C_{1-4}$)alkyl, —C(O)O—$C_{1-4}$ alkyl, —C(O)NH—$C_{1-4}$ alkyl, $C_{1-4}$ alkylamino, and di($C_{1-4}$) alkylamino. Most preferably, $R^{53}$–$R^{58}$ are independently selected from the group consisting of hydrogen, fluoro, chloro, bromo, trifluoromethyl, hydroxy, hydroxymethyl, hydroxyethyl, nitro, cyano, methoxy, and carboxy.

Also, one group of useful compounds of the invention are compounds of Formula VI:

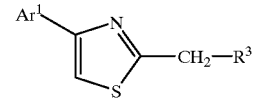

(VI)

or a solvate, hydrate or a pharmaceutically acceptable salt thereof, wherein

Ar¹ and R³ are as defined for Formula I.

Useful compounds of the present invention include, without limitation:

1. 3-{[4-(5,5,8,8-tetramethyl-2-5,6,7,8-tetrahydronaphthyl)-1,3-thiazol-2-yl]amino}phenol;
2. 4-{[4-(3-ethyl-5,5,8,8-tetramethyl-2-5,6,7,8-tetrahydronaphthyl)-1,3-thiazol-2-yl]amino}benzoic acid;
3. 3-{4-(3-ethyl-5,5,8,8-tetramethyl-2-5,6,7,8-tetrahydronaphthyl)-1,3-thiazol-2-yl]amino}benzoic acid;
4. [4-(3-bromophenyl)(1,3-thiazol-2-yl)][3-(trifluoromethyl)phenyl]amine;
5. (3,5-dichlorophenyl)[4-(4-fluorophenyl)(1,3-thiazol-2-yl)]amine;
6. [4-(4-bromophenyl)(1,3-thiazol-2-yl)](3-chlorophenyl)amine;
7. [4-(3,4-dichlorophenyl)(1,3-thiazol-2-yl)](2,5-difluorophenyl)amine;
8. (3,5-dichlorophenyl){4-[4-(trifluoromethyl)phenyl](1,3-thiazol-2-yl}amine;
9. 2-{[4-(4-phenylphenyl)-1,3-thiazol-2-yl]amino}phenol;
10. 4-{[4-(4-bromophenyl)-1,3-thiazol-2-yl]amino}benzenecarbonitrile;
11. 4-{[4-(4-phenylphenyl)-1,3-thiazol-2-yl]amino}benzenecarbonitrile;
12. (2,4-difluorophenyl)[4-(4-chlorophenyl)-5-phenyl-1,3-thiazol-2-yl]amine;
13. 4-{[4-(4-phenylphenyl)-1,3-thiazol-2-yl]amino}-1,2,3-trifluorobenzene;
14. [4-(3,4-difluorophenyl)(1,3-thiazol-2-yl)](3,4-dichlorophenyl)amine;
15. [4-(4-trifluoromethylphenyl)(1,3-thiazol-2-yl)](4-nitrophenyl)amine;
16. [4-(3,4-difluorophenyl)(1,3-thiazol-2-yl) (3,5-dichlorophenyl)amine;
17. [4-(3,4-difluorophenyl)(1,3-thiazol-2-yl)](3-chloro-4-bromophenyl)amine;

18. [4-(3,4-difluorophenyl)(1,3-thiazol-2-yl)](3-trifluoromethylphenyl)amine;
19. [4-(2,4-difluorophenyl)(1,3-thiazol-2-yl)](3,4-dichlorophenyl)amine;
20. 4-{4-(3-ethyl-5,5,8,8-tetramethyl-2-5,6,7,8-tetrahydronaphthyl)-1,3-thiazol-2-yl]amino}-1-hydroxyethylbenzene;
21. 2-{[4-(5,5,8,8-tetramethyl-2-5,6,7,8-tetrahydronaphthyl)-1,3-thiazol-2-yl]amino}phenol;
22. [4-(4-trifluoromethylphenyl)(1,3-thiazol-2-yl)](3,4-dichlorophenyl)amine;
23. 4-{[4-(2,4-dichlorophenyl)-1,3-thiazol-2-yl]amino}benzenecarbonitrile;
24. (4-aminophenyl)[4-(4-chlorophenyl)-5-(4-methylphenyl)-1,3-thiazol-2-yl]amine;
25. [4-(2,4-difluorophenyl)(1,3-thiazol-2-yl)](3,5-dichlorophenyl)amine;
26. [4-(4-trifluoromethylphenyl)(1,3-thiazol-2-yl)](3-hydroxyphenyl)amine;
27. [4-(4-tert-butyl-2,6-dimethyl-3,5-dinitrophenyl)(1,3-thiazol-2-yl)](3,4,5-trimethoxypheny)amine;
28. 3-[4-(4-tert-butyl-2,6-dimethyl-3,5-dinitrophenyl)(1,3-thiazol-2-yl)amino]benzoic acid;
29. 3-[4-(4-tert-butyl-2,6-dimethyl-3,5-dinitrophenyl)(1,3-thiazol-2-yl)amino]phenol;
30. [4-(4-nitrophenyl)(1,3-thiazol-2-yl)](4-benzyloxyphenyl)amine;
31. [4-(4-nitrophenyl)(1,3-thiazol-2-yl)](2,4-dimethoxyphenyl)amine;
32. [4-(4-fluorophenyl)(1,3-thiazol-2-yl)](3,4-dichlorophenyl)amine;
33. [4-(4-chlorophenyl)(1,3-thiazol-2-yl)](3-hydroxyphenyl)amine;
34. [4-(3-chloro-4-methylphenyl)-5-methyl-1,3-thiazol-2-yl](3-hydroxyphenyl)amine;
35. (4-nitrophenyl)[4-(isoxazol-3-yl-5-carboxylic acid ethyl ester)-1,3-thiazol-2-yl]amine;
36. (2,4,5-trichlorophenyl)[4-(isoxazol-3-yl-5-carboxylic acid ethyl ester)-1,3-thiazol-2-yl]amine; and
37. 2-cyanomethyl-4-(5,5,8,8-tetramethyl-2-5,6,7,8-tetrahydronaphthyl)-1,3-thiazole.

It is also to be understood that the present invention is considered to include stereoisomers as well as optical isomers, e.g. mixtures of enantiomers as well as individual enantiomers and diastereomers, which arise as a consequence of structural asymmetry in selected compounds of the present series. The methods for separating the individual enantiomers are known to those skilled in the art.

Also, included within the scope of the present invention are the non-toxic pharmaceutically acceptable salts of the compounds of the present invention. Examples of pharmaceutically acceptable salts include inorganic and organic acid addition salts such as hydrochloride, hydrobromide, phosphate, sulphate, citrate, lactate, tartrate, maleate, fumarate, mandelate, acetic acid, dichloroacetic acid and oxalate. Acid addition salts are formed by mixing a solution of a particular aminothiazole of the present invention with a solution of a pharmaceutically acceptable non-toxic acid, such as hydrochloric acid, hydrobromic acid, fumaric acid, maleic acid, succinic acid, acetic acid, citric acid, tartaric acid, carbonic acid, phosphoric acid, oxalic acid, dichloroacetic acid, and the like. Basic salts are formed by mixing a solution of the thiazole compound of the present invention with a solution of a pharmaceutically acceptable non-toxic base, such as sodium hydroxide, potassium hydroxide, choline hydroxide, sodium carbonate, and the like.

The compounds of Formula I may also be solvated, especially hydrated. Hydration may occur during manufacturing of the compounds or compositions comprising the compounds, or the hydration may occur over time due to the hygroscopic nature of the compounds.

The term "aryl" as employed herein by itself or as part of another group refers to monocyclic or bicyclic aromatic groups containing from 6 to 12 carbons in the ring portion, such as phenyl, biphenyl, naphthyl or tetrahydronaphthyl. Preferably, the aryl group contains 6–10 carbons in the ring portion.

The term "heteroaryl" as employed herein refers to groups having 5 to 14 ring atoms; 6, 10 or 14 π electrons shared in a cyclic array; and containing carbon atoms and 1, 2 or 3 oxygen, nitrogen or sulfur heteroatoms (where examples of heteroaryl groups are: thienyl, benzo[b]thienyl, naphtho[2,3-b]thienyl, thianthrenyl, furyl, benzofuryl, pyranyl, isobenzofuranyl, benzoxazolyl, chromenyl, xanthenyl, phenoxathiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, 4aH-carbazolyl, carbazolyl, β-carbolinyl, phenanthridinyl, acridinyl, perimidinyl, phenanthrolinyl, phenazinyl, thiazolyl, isothiazolyl, phenothiazinyl, isoxazolyl, furazanyl and phenoxazinyl groups).

The term "alkyl" as employed herein by itself or as part of another group refers to both straight and branched chain radicals of up to 12 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl. Preferably, the alkyl chain is 1 to 6 carbon atoms in length, more preferably 1 to 4 carbon atoms in length.

The term "cycloalkyl" as employed herein by itself or as part of another group refers to cycloalkyl groups containing 3 to 9 carbon atoms, preferably 3 to 7 carbon atoms. Typical examples are cyclopropyl, cyclobutyl, cyclopentyl, cyclohexyl, cycloheptyl, cyclooctyl and cyclononyl.

The term "aroyl" as employed herein refers to the radical R—CO—, wherein R is any of the above aryl and heteroaryl groups.

Useful halogen groups include fluorine, chlorine, bromine and iodine.

Useful haloalkyl groups include $C_{1-12}$ alkyl groups substituted by one or more fluorine, chlorine, bromine or iodine atoms, e.g., fluoromethyl, difluoromethyl, trifluoromethyl, pentafluoroethyl, 1,1-difluoroethyl and trichloromethyl groups.

Useful hydroxyalkyl groups include $C_{1-12}$ alkyl groups substituted by hydroxy, e.g., hydroxymethyl, hydroxyethyl, hydroxypropyl and hydroxybutyl groups.

Useful alkoxy groups include oxygen substituted by one of the $C_{1-12}$ alkyl groups mentioned above.

Useful acylamino groups are any acyl group, particularly $C_{2-6}$ alkanoyl or $C_{6-10}$ aryl($C_{2-6}$)alkanoyl attached to an amino nitrogen, e.g., acetamido, propionamido, butanoylamido, pentanoylamido, hexanoylamido, and benzoylamido.

Useful acyloxy groups are any $C_{1-6}$ acyl (alkanoyl) attached to an oxy (—O—) group, e.g., acetoxy, propionyloxy, bytanoyloxy, pentanoyloxy, hexanoyloxy and the like.

Useful alkylamino and dialkylamino groups are —$NHR^6$ and —$NR^6R^7$, wherein $R^6$ and $R^7 C_{1-6}$ alkyl groups.

Optional substituents on $Ar^1$, $Ar^{21}$, $Ar^{31}$, $Ar^2$, $Ar^{22}$, $R^1$ and $R^3$ include any one of halogen, haloalkyl, cycloalkyl, alkyl, cycloalkylalkyl, hydroxyalkyl, carboxyalkyl, alkoxyalkyl, nitro, amino, cyano, acylamino, hydroxy, thiol, acyloxy, alkoxy, carboxy, —C(O)O-alkyl, —O—C(O)-alkyl, —C(O)NH-alkyl, aryloxy, arylalkyloxy, —NHR$^4$, —NR$^4$R$^5$ wherein R$^4$ and R$^5$ are selected from the group consisting of C$_{1-6}$ alkyl, —C(O)(C$_{1-6}$)alkyl, aroyl, —C(O)NH(C$_{1-3}$)alkyl and —C(O)NH-aryl. More preferably the optional substituents include halogen, halo(C$_{1-6}$)alkyl, cycloalkyl, C$_{1-6}$ alkyl, cycloalkyl(C$_{1-6}$)alkyl, hydroxy(C$_{1-6}$)alkyl, carboxy(C$_{1-6}$) alkyl, C$_{1-6}$ alkoxy(C$_{1-6}$)alkyl, nitro, amino, cyano, C$_{1-6}$ acylamino, hydroxy, thiol, C$_{1-6}$ acyloxy, C$_{1-6}$ alkoxy, carboxy, di(C$_{1-6}$)alkylamino, —C(O)O(C$_{1-3}$)alkyl, —O—C(O)(C$_{1-3}$)alkyl, —C(O)NH(C$_{1-3}$)alkyl, aryloxy, aryl(C$_{1-6}$)oxy, —NHR$^4$, wherein R$^4$ is selected from the group consisting of C$_{1-6}$ alkyl, —C(O)(C$_{1-6}$)alkyl, aroyl, —C(O)NH(C$_{1-3}$)alkyl and —C(O)NH-aryl.

The compounds of the invention may be prepared using methods known for the skilled person in the art. For example, compounds of Formula I, wherein Y is —N— or —C(R$^3$)— can be prepared by allowing a bromoketone of the Formula VII:

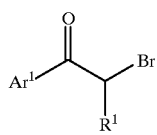

(VII)

wherein Ar$^1$ and R$^1$ are as defined above, to react with a mono- or -di-substituted thiourea of Formula VIII:

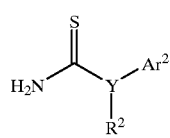

(VIII)

wherein Ar$^2$, R$^2$ and R$^3$ are as defined above, in an appropriate solvent, such as acetone or DMF, for a sufficient time period.

Compounds of Formula I, wherein Y is —CH(R$^3$)— can be prepared by allowing a bromoketone of the Formula VII to react with a thiourea of Formula IX:

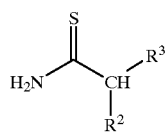

(IX)

wherein R$^2$ and R$^3$ are as defined above, in an appropriate solvent for a sufficient time period.

The starting materials, e.g., the compounds of Formula VII, VIII and IX are either known or may be produced in known manner or analogous to the methods described herein.

PAI-1 Assay

The inhibitory activity of PAI-1 against uPA was measured by a direct chromogenic assay using the substrate N-CBZ-VAL-GLY-ARG p-nitroanilide. The tested compound was added to PAI-1 which had been diluted in activity assay buffer (0.05M Hepes, pH 7.5, 0.15M NaCl, containing 0.05% N-octyl-D-glucopyranoside and 250 µg/ml bovine serum albumin). After a 10 minute incubation at 37° C., uPA was added (0.04 units/assay), followed immediately by the addition of substrate. After reequilibration at 37° C., residual uPA activity was quantified by measuring the change in absorbance at 405 nm over 12 minutes. The concentration of active PAI-1 in the assays was the amount required to inhibit 80–85% of uPA as compared to samples containing uPA alone.

Compositions within the scope of the invention include all compositions wherein the compounds of the present invention are contained in an amount that is effective to achieve its intended purpose. While individual needs vary, determination of optimal ranges of effective amounts of each component is within the skill of the art. Typically, the compounds may be administered to mammals, e.g., humans, orally at a dose of 1 to 1000 mg/kg, or an equivalent amount of the pharmaceutically acceptable salt thereof, per day of the body weight of the mammal being treated for thrombosis, angina pectoris, cerebral infarction, myocardial infarction, pulmonary infarction, intra-atrial thrombus in atrial fibrillation, deep venous thrombus, disseminated intravascular coagulation syndrome, diabetic complications, restenosis after percutaneous transluminal coronary angioplasty and stroke. For intramuscular injection, the dose is generally about one-half of the oral dose.

The unit oral dose may comprise from about 1 to about 1000 mg, preferably about 1 to about 100 mg of the compound. The unit dose may be administered one or more times daily as one or more tablets each containing from about 0.1 to about 50, conveniently about 0.25 to about 100 mg of the compound or its solvates.

In addition to administering the compound as a raw chemical, the compounds of the invention may be administered as part of a pharmaceutical preparation containing suitable pharmaceutically acceptable carriers comprising excipients and auxiliaries which facilitate processing of the compounds into preparations which can be used pharmaceutically. Preferably, the preparations, particularly those preparations which can be administered orally and which can be used for the preferred type of administration, such as tablets, dragees, and capsules, and also preparations which can be administered rectally, such as suppositories, as well as suitable solutions for administration by injection or orally, containing from about 0.01 to 99 percent, preferably from about 0.25 to about 75 percent of active compound(s), together with the excipient.

The pharmaceutical compositions of the invention may be administered to any animal that may experience the beneficial effects of the compounds of the invention. Foremost among such animals are mammals, e.g. humans, although the invention is not intended to be so limited.

The pharmaceutical compositions of the invention may be administered by any means that achieve their intended purpose. For example, administration may be parenteral, subcutaneous, intravenous, intramuscular, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the desired effect.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers, such as saccharides, for example, lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof such as magnesium stearate or calcium stearate, and/or polyethylene glycol. Dragee cores are provided with suitable coatings which, if desired, are resistant to gastric juices. For this purpose, concentrated saccharine solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations, such as acetylcellulose phthalate or hydroxypropylmethylcellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations, which can be used rectally, include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions may contain substances which increase the viscosity of the suspension, and include, for example, sodium carboxymethyl cellulose, sorbitol, and/or dextran. Optionally, the suspension may also contain stabilizers.

The following examples are illustrative, but not limiting, of the method and compositions of the present invention. Other suitable modifications and adaptations of the variety of conditions and parameters normally encountered in clinical therapy and which are obvious to those skilled in the art within the spirit and scope of the invention.

EXAMPLE 1

The following compounds were prepared according to the method described above by suspending a solution of a suitably substituted thiourea or thioamide (2 mmol) and a suitably substituted α-haloketone (2 mmol) in acetone and then heating the suspension to reflux at 55° C. for 12 hours. The product precipitated as a white solid. The product was filtrated and washed with cold acetone to afford the pure product as a white solid.

In cases where the product did not precipitate, the solvent was removed under reduced pressure to give the pure 2-substituted thiazole as a white solid.

3-{[4-(5,5,8,8-tetrametyl-2-5,6,7,8-tetrahydronaphtyl)-1,3-thiazol-2-yl]amino}phenol; $^1$H NMR (δ, DMSO): 1.26 (s, 6H), 1.30 (s, 6H), 1.66 (s, 4H), 6.43 (d, 1H), 7.04–7.82 (m, 7H); MS: M+1=379 (calculated 378).

4-{[4-(3-ethyl-5,5,8,8-tetramethyl-2-5,6,7,8-tetrahydronaphtyl)-1,3-thiazol-2-yl]amino}benzoic acid; $^1$H NMR (δ, DMSO): 1.08–1.12 (t, 3H), 1.25 (s, 6H), 1.26 (s, 6H), 1.64 (s, 4H), 2.73–2.79 (m, 2H), 6.94 (s, 1H), 7.20–7.87 (m, 6H); MS: M+1=435 (calculated 434).

3-{[4-(3-ethyl-5,5,8,8-tetramethyl-2-5,6,7,8-tetrahydronapthyl)-1,3-thiazol-2-yl]amino}benzoic acid; $^1$H NMR (δ, DMSO): 1.08–1.12 (t, 3H), 1.26 (s, 6H), 1.27 (s, 6H), 1.65 (s, 4H), 2.76–2.81 (m, 2H), 6.89 (s, 1H), 7.21–8.34 (m, 6H); MS: M+1=435 (calculated 434).

[4-(3-bromophenyl)-1,3-thiazol-2-yl][3-(trifluoromethyl)-phenylamine; $^1$H NMR (δ, DMSO):7.30–8.46 (m, 9H), 10.74 (s, 1H); MS: M+1=399 (calculated 398).

(3,5-dichlorophenyl)[4-(4-fluorophenyl)(1,3-thiazol-2yl)]amine; $^1$H NMR (δ, DMSO): 7.12–7.94 (m, 9H), 10.80 (s, 1H); MS: M+1=339, M+3=341 (calculated 338).

[4-(4-bromophenol)(1,3-thiazol-2-yl)](3-chlorophenyl)amine: $^1$HNMR (δ, DMSO): 6.98–7.92 (m, 9H); MS: M+1=365, M+3=367 (calculated 364).

[4-(3,4-dichlorophenyl)(1,3-thiazol-2-yl)](2,5-difluorophenyl)amine: $^1$H NMR (δ, DMSO): 6.80–6.84 (t, 1H), 7.28–7.34 (m, 1H), 7.67–8.53 (m, 5H), 10.44 (s, 1H); MS: M+1=359, M+3=359 (calculated 356).

(3,5-dichlorophenyl){4-[4-(trifluoromethyl)phenyl](1,3-thiazol-2-yl)}amine; $^1$H NMR (δ, DMSO): 7.12–7.15 (m, 1H), 7.68–7.87 (m, 5H), 8.07–8.09 (d, 2H), 10.80 (s, 1H); MS: M+1=389, M+3=391 (calculated 388).

4-{[4-(4-bromophenyl)-1,3-thiazol-2-yl amino}benzenecarbonitrile; $^1$H NMR (δ, DMSO): 7.58 (s, 1H), 7.62–7.65 (m, 2H), 7.78–7.82 (m, 2H), 7.89–7.96 (m, 4H), 11.01 (s, 1H); MS: M+1=356, M+3=358 (calculated 355).

4-{[4-(4-phenylphenyl)-1,3-thiazol-2-yl]amino}benzenecarbonitrile; $^1$H NMR (δ, CDCl$_3$): 6.92 (s, 1H), 7.38–7.85 (m, 13H), 11.61 (s, 1H); MS: M+1=354 (calculated 353).

EXAMPLE 2

Optionally substituted thiourea or thioamide (0.075 mmol) in DMF (0.25 mL) and an optionally substituted α-haloketone in DMF (0.25 mL) were added to a 2 mL Robbins 96 well plate. The reaction mixture was shaken for 2 days at 75° C., and subsequently the solvent was evaporated to dryness using a Savant speedvac to give the pure 2-substituted thiazole.

EXAMPLE 3

Activity of Compounds 1 to 37 as PAI-1 Inhibitors

Compounds No. 1 to 37 were tested in the PAI-1 assay as described above. The compounds exhibited PAI-1 inhibitory activity in vitro with IC$_{50}$ value of between 1.1 and 18.5 μM. Compound 3 had an IC$_{50}$ value of 1.1 μM, compound 11 had an IC$_{50}$ value of 1.6 μM, and compound 2 had an IC$_{50}$ value of 1.8 μM.

Those skilled in the art will recognize that while specific embodiments have been illustrated and described, various modifications and changes may be made without departing from the spirit and scope of the invention.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims. All publications, patent applications and patents cited herein are fully incorporated by reference.

What is claimed is:

1. A method for prophylaxis or treatment of thrombosis, angina pectoris, cerebral infarction, myocardial infarction, pulmonary infarction, intra-atrial thrombus in atrial fibrillation, deep venous thrombus, disseminated intravascular coagulation syndrome, diabetic complications, restenosis and stroke, comprising administering to a mammal in need thereof an effective amount of a compound of Formula I:

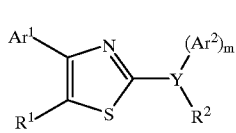

(I)

or a solvate, hydrate or a pharmaceutically acceptable salt thereof, wherein

Y is —N—;

Ar$^1$ is an optionally substituted aryl or heteroaryl radical;
Ar$^2$ is an optionally substituted aryl or heteroaryl radical, wherein heteroaryl is selected from the group consisting of thienyl, benzothienyl, furyl, benzofuryl, thiazolyl, imidazolyl, isoxazolyl, pyrrolyl and pyrazolyl;
m is 1;
R$^1$ is selected from the group consisting of hydrogen, alkyl, cycloalkyl, and aryl or heteroaryl radical, all of which can be optionally substituted; and
R$^2$ is hydrogen, or an optionally substituted aryl or an optionally substituted heteroaryl radical;
with the provisos that
when R$^1$ and R$^2$ are hydrogen and Ar$^2$ is an optionally substituted phenyl, then Ar$^1$ is other than a phenyl group substituted with carboxyalkyl or an alkyl ester of carboxyalkyloxy;
when R$^1$ is hydrogen, and Ar$^2$ and R$^2$ are both a phenyl group, then Ar$^1$ is other than a phenyl group substituted with carboxyalkyl; or
when R$^1$ and R$^2$ are hydrogen and Ar$^2$ is naphthyl, then Ar$^1$ is other than a phenyl group substituted with carboxyalkyl.

2. The method according to claim 1, wherein Ar$^1$ and Ar$^2$ are independently selected from the group consisting of phenyl, biphenyl, naphthyl, tetrahydronaphthyl, thienyl, benzothienyl, furyl, benzofuryl, thiazolyl, imidazolyl, isoxazolyl, pyrrolyl and pyrazolyl, any of which can be optionally substituted.

3. The method according to claim 1, wherein R$^1$ and R$^2$ both are hydrogen.

4. The method according to claim 1, wherein the compound administered is a compound of Formula II:

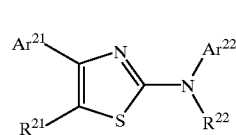

(II)

or a solvate, hydrate or a pharmaceutically acceptable salt thereof, wherein

Ar$^{21}$ is an optionally substituted aryl or an optionally substituted heteroaryl radical;
Ar$^{22}$ is a substituted aryl;
R$^{21}$ is selected from the group consisting of hydrogen, alkyl, cycloalkyl, and aryl or heteroaryl radical, all of which can be optionally substituted;
R$^{22}$ is hydrogen, or an optionally substituted aryl or an optionally substituted heteroaryl radical,
with the provisos that
when R$^{21}$ and R$^{22}$ are hydrogen and Ar$^{22}$ is substituted phenyl, then Ar$^{21}$ is other than a phenyl group substituted with carboxyalkyl;
when R$^{21}$ is hydrogen, and Ar$^{22}$ and R$^{22}$ are both a phenyl group, then Ar$^{21}$ is other than a phenyl group substituted with carboxyalkyl; or
when R$^{21}$ and R$^{22}$ are hydrogen and Ar$^{22}$ is naphthyl, then Ar$^{21}$ is other than a phenyl group substituted with carboxyalkyl.

5. The method according to claim 4, wherein the aryl or heteroaryl radical is selected from the group consisting of phenyl, biphenyl, naphthyl, tetrahydronapthyl and isoxazolyl.

6. The method according to claim 4, wherein the compound administered is a compound of Formula III:

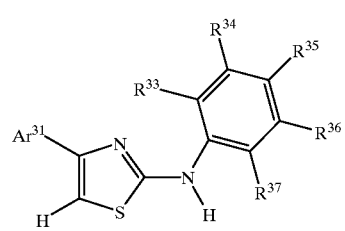

(III)

or a solvate, hydrate or a pharmaceutically acceptable salt thereof, wherein

Ar$^{31}$ is an optionally substituted aryl or an optionally substituted heteroaryl radical selected from the group consisting of biphenyl, naphthyl, tetrahydronaphthyl and isoxazolyl; and
R$^{33}$–R$^{37}$ are independently selected from the group consisting of hydrogen, alkyl, halogen, haloalkyl, hydroxy, hydroxyalkyl, amino, aminoalkyl, alkoxy, alkoxyalkyl, nitro, cyano, thiol, alkylthiol, acylamino, acyloxy, carboxy, carboxyalkyl, —C(O)O-alkyl, —C(O)NH-alkyl, —NHR$^4$, —NR$^4$R$^5$, phenoxy, and phenyl(C$_{1-4}$) alkyloxy, wherein R$^4$ is selected from the group consisting of alkyl, —C(O)O-alkyl, aroyl, —C(O)NH-alkyl and —C(O)NH-aryl, provided that at least one of R$^{33}$–R$^{37}$ is other than hydrogen.

7. The method according to claim 4, wherein the compound administered is a compound of Formula IV:

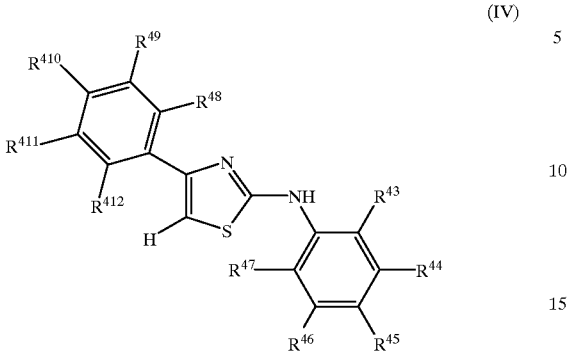

(IV)

or a solvate, hydrate or a pharmaceutically acceptable salt thereof, wherein at least one of $R^{48}$–$R^{412}$ is trifluoro($C_{1-6}$)alkyl and the substituents that are not trifluoro($C_{1-6}$)alkyl are independently selected from the group consisting of hydrogen, $C_{1-6}$ alkyl, halogen, halo($C_{1-6}$)alkyl, hydroxy, hydroxy($C_{1-6}$)alkyl, amino, amino($C_{1-6}$)alkyl, $C_{1-6}$ alkoxy, $C_{1-6}$ alkoxy($C_{1-6}$)alkyl, nitro, cyano, thiol, $C_{1-6}$ alkylthiol, $C_{1-6}$ acylamino, $C_{1-6}$ acyloxy, carboxy, carboxy($C_{1-6}$)alkyl, —C(O)O—$C_{1-6}$ alkyl, —C(O)NH—$C_{1-6}$ alkyl, $C_{1-6}$ alkylamino, di($C_{1-6}$)alkylamino, phenoxy, benzyloxy, —C(O)O($C_{1-3}$)alkyl, —O—C(O)($C_{1-3}$)alkyl, and —NHC(O)($C_{1-3}$)alkyl; and $R^{43}$–$R^{47}$ are independently selected from the group consisting of hydrogen, $C_{1-6}$ alkyl, halogen, halo($C_{1-6}$)alkyl, hydroxy, hydroxy($C_{1-6}$)alkyl, amino, amino($C_{1-6}$)alkyl, $C_{1-6}$ alkoxy, $C_{1-6}$ alkoxy($C_{1-6}$)alkyl, nitro, cyano, thiol, $C_{1-6}$ alkylthiol, $C_{1-6}$ acylamino, $C_{1-6}$ acyloxy, carboxy, carboxy($C_{1-6}$)alkyl, —C(O)O—$C_{1-6}$ alkyl, —C(O)NH—$C_{1-6}$ alkyl, $C_{1-6}$ alkylamino, di($C_{1-6}$)alkylamino, phenoxy, and benzyloxy, —C(O)O($C_{1-3}$)alkyl, —O—C(O)($C_{1-3}$)alkyl, and —NHC(O)($C_{1-3}$)alkyl, provided that at least one of $R^{43}$–$R^{47}$ is other than hydrogen.

8. The method according to claim 4, wherein the compound administered is a compound of Formula IV:

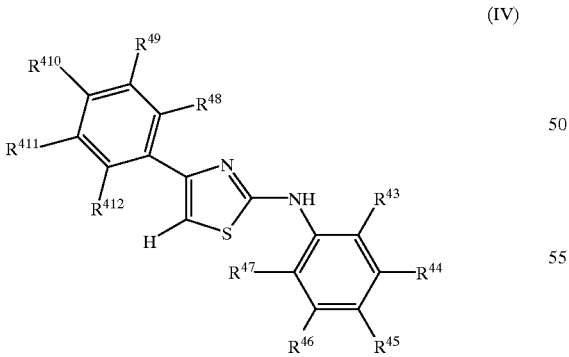

(IV)

or a solvate, hydrate or a pharmaceutically acceptable salt thereof, wherein
at least one of $R^{48}$–$R^{412}$ is nitro and the substituents that are not nitro are independently selected from the group consisting of hydrogen, $C_{1-6}$ alkyl, halogen, halo($C_{1-6}$)alkyl, hydroxy, hydroxy($C_{1-6}$)alkyl, amino, amino($C_{1-6}$)alkyl, $C_{1-6}$ alkoxy, $C_{1-6}$ alkoxy($C_{1-6}$)alkyl, cyano, thiol, $C_{1-6}$ alkylthiol, $C_{1-6}$ acylamino, $C_{1-6}$ acyloxy, carboxy, carboxy($C_{1-6}$)alkyl, —C(O)O—$C_{1-6}$ alkyl, —C(O)NH—$C_{1-6}$ alkyl, $C_{1-6}$ alkylamino, di($C_{1-6}$)alkylamino, phenoxy, benzyloxy, —C(O)O($C_{1-3}$)alkyl, —O—C(O)($C_{1-3}$)alkyl, and —NHC(O)($C_{1-3}$)alkyl; and $R^{43}$–$R^{47}$ are independently selected from the group consisting of hydrogen, $C_{1-6}$ alkyl, halogen, halo($C_{1-6}$)alkyl, hydroxy, hydroxy($C_{1-6}$)alkyl, amino, amino($C_{1-6}$)alkyl, $C_{1-6}$ alkoxy, $C_{1-6}$ alkoxy($C_{1-6}$)alkyl, cyano, $C_{1-6}$ alkylthiol, $C_{1-6}$ acylamino, $C_{1-6}$ acyloxy, carboxy, —C(O)O—$C_{1-6}$ alkyl, —C(O)NH—$C_{1-6}$ alkyl, $C_{1-6}$ alkylamino, di-$C_{1-6}$ alkylamino, phenoxy, benzyloxy, —C(O)O($C_{1-3}$)alkyl, —O—C(O)($C_{1-3}$)alkyl, and —NHC(O)($C_{1-3}$)alkyl, provided that at least one of $R^{43}$–$R^{47}$ is other than hydrogen.

9. The method according to claim 4, wherein the compound administered is a compound of Formula IV:

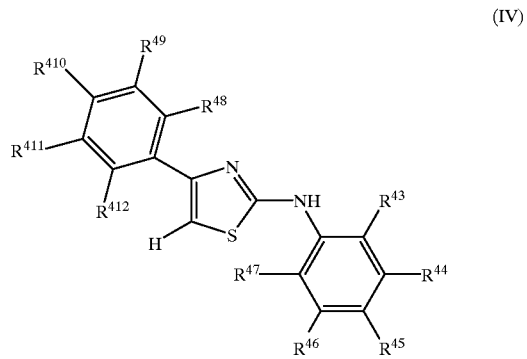

(IV)

or a solvate, hydrate or a pharmaceutically acceptable salt thereof, wherein at least one of $R^{43}$–$R^{47}$ is cyano and the substitutents that are not cyano are independently selected from the group consisting of hydrogen, $C_{1-6}$ alkyl, halogen, halo($C_{1-6}$)alkyl, hydroxy, hydroxy($C_{1-6}$)alkyl, amino ($C_{1-6}$)alkyl, $C_{1-6}$ alkoxy, $C_{1-6}$ alkoxy($C_{1-6}$)alkyl, $C_{1-6}$ alkylthiol, $C_{1-6}$ acylamino, $C_{1-6}$ acyloxy, carboxy, —C(O)O—$C_{1-6}$ alkyl, —C(O)NH—$C_{1-6}$ alkyl, $C_{1-6}$ alkylamino, di($C_{1-6}$)alkylamino, phenoxy, benzyloxy, —C(O)O($C_{1-3}$)alkyl, —O—C(O)($C_{1-3}$)alkyl, and —NHC(O)($C_{1-3}$)alkyl; and $R^{48}$–$R^{412}$ are independently selected from the group consisting of hydrogen, $C_{1-6}$ alkyl, halogen, halo($C_{1-6}$)alkyl, hydroxy, hydroxy($C_{1-6}$)alkyl, amino, amino($C_{1-6}$)alkyl, $C_{1-6}$ alkoxy, $C_{1-6}$ alkoxy($C_{1-6}$)alkyl, nitro, cyano, thiol, $C_{1-6}$ alkylthiol, $C_{1-6}$ acylamino, $C_{1-6}$ acyloxy, carboxy, carboxy($C_{1-6}$)alkyl, —C(O)O—$C_{1-6}$ alkyl, —C(O)NH—$C_{1-6}$ alkyl, $C_{1-6}$ alkylamino, di($C_{1-6}$)alkylamino, phenoxy, benzyloxy, —C(O)O($C_{1-3}$)alkyl, —O—C(O)($C_{1-3}$)alkyl, and —NHC(O)($C_{1-3}$)alkyl.

10. The method according to claim 1, wherein the compound administered is a compound of Formula V:

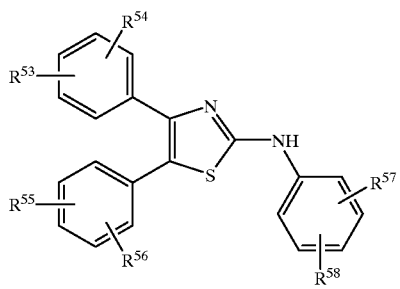

(V)

or a solvate, hydrate or a pharmaceutically acceptable salt thereof, wherein $R^{53}$–$R^{58}$ are independently selected from the group insisting of hydrogen, alkyl, halogen, haloalkyl, hydroxy, hydroxyalkyl, amino, aminoalkyl, alkoxy, alkoxyalkyl, nitro, cyano, thiol, alkylthiol, acylamino, acyloxy, carboxy, carboxyalkyl, —C(O)O-alkyl, —C(O)NH-alkyl, —NHR$^4$, —NR$^4$R$^5$, phenoxy, and benzyloxy, wherein R$^4$ is selected from the group consisting of alkyl, —C(O)O-alkyl, aroyl, —C(O)NH-alkyl and —C(O)NH-aryl.

11. The method according to claim 1, wherein the compound administered is selected from the group consisting of
3-{[4-(5,5,8,8-tetramethyl-2-5,6,7,8-tetrahydronaphthyl)-1,3-thiazol-2-yl]amino}phenol;
4-{[4-(3-ethyl-5,5,8,8-tetramethyl-2-5,6,7,8-tetrahydronaphthyl)-1,3-thiazol-2-yl]amino}benzoic acid;
3-{4-(3-ethyl-5,5,8,8-tetramethyl-2-5,6,7,8-tetrahydronaphthyl)-1,3-thiazol-2-yl]amino}benzoic acid;
[4-(3-bromophenyl)(1,3-thiazol-2-yl)][3-(trifluoromethyl)phenyl]amine;
(3,5-dichlorophenyl)[4-(4-fluorophenyl)(1,3-thiazol-2-yl)]amine;
[4-(4-bromophenyl)(1,3-thiazol-2-yl)](3-chlorophenyl)amine;
[4-(3,4-dichlorophenyl)(1,3-thiazol-2-yl)](2,5-difluorophenyl)amine;
(3,5-dichlorophenyl){4-[4-(trifluoromethyl)phenyl](1,3-thiazol-2-yl}amine;
2-{[4-(4-phenylphenyl)-1,3-thiazol-2-yl]amino}phenol;
4-{[4-(4-bromophenyl)-1,3-thiazol-2-yl]amino}-benzenecarbonitrile;
4-{[4-(4-phenylphenyl)-1,3-thiazol-2-yl]amino}-benzenecarbonitrile;
(2,4-difluorophenyl)[4-(4-chlorophenyl)-5-phenyl-1,3-thiazol-2-yl]amine;
4-{[4-(4-phenylphenyl)-1,3-thiazol-2-yl]amino}-1,2,3-trifluorobenzene;
[4-(3,4-difluorophenyl)(1,3-thiazol-2-yl)](3,4-dichlorophenyl)-amine;
[4-(4-trifluoromethylphenyl)(1,3-thiazol-2-yl)](4-nitrophenyl)amine;
[4-(3,4-difluorophenyl)(1,3-thiazol-2-yl)](3,5-dichlorophenyl)amine;
[4-(3,4-difluorophenyl)(1,3-thiazol-2-yl)](3-chloro-4-bromophenyl)amine;
[4-(3,4-difluorophenyl)(1,3-thiazol-2-yl)](3-trifluoromethylphenyl)amine;
[4-(2,4-difluorophenyl)(1,3-thiazol-2-yl)](3,4-dichlorophenyl)amine;
4-{4-(3-ethyl-5,5,8,8-tetramethyl-2-5,6,7,8-tetrahydronaphthyl)-1,3-thiazol-2-yl]amino}-1-hydroxyethylbenzene;
2-{[4-(5,5,8,8-tetramethyl-2-5,6,7,8-tetrahydronaphthyl)-1,3-thiazol-2-yl]amino}phenol;
[4-(4-trifluoromethylphenyl)(1,3-thiazol-2-yl)](3,4-dichlorophenyl)amine;
4-{[4-(2,4-dichlorophenyl)-1,3-thiazol-2-yl]amino}benzenecarbonitrile;
(4-aminophenyl)[4-(4-chlorophenyl)-5-(4-methylphenyl)-1,3-thiazol-2-yl]amine;
[4-(2,4-difluorophenyl)(1,3-thiazol-2-yl)](3,5-dichlorophenyl)amine;
[4-(4-trifluoromethylphenyl)(1,3-thiazol-2-yl)](3-hydroxyphenyl)amine;
[4-(4-tert-butyl-2,6-dimethyl-3,5-dinitrophenyl)(1,3-thiazol-2-yl)](3,4,5-trimethoxyphenyl)amine;
3-[4-(4-tert-butyl-2,6-dimethyl-3,5-dinitrophenyl)(1,3-thiazol-2-yl)amino]benzoic acid;
3-[4-(4-tert-butyl-2,6-dimethyl-3,5-dinitrophenyl)(1,3-thiazol-2-yl)amino]phenol;
[4-(4-nitrophenyl)(1,3-thiazol-2-yl)](4-benzyloxyphenyl)amine;
[4-(4-nitrophenyl)(1,3-thiazol-2-yl)](2,4-dimethoxyphenyl)amine;
[4-(4-fluorophenyl)(1,3-thiazol-2-yl)](3,4-dichlorophenyl)amine;
[4-(4-chlorophenyl)(1,3-thiazol-2-yl)](3-hydroxyphenyl)amine;
[4-(3-chloro-4-methylphenyl)-5-methyl-1,3-thiazol-2-yl](3-hydroxyphenyl)amine;
(4-nitrophenyl)[4-(isoxazol-3-yl-5-carboxylic acid ethyl ester)-1,3-thiazol-2-yl]amine; and
(2,4,5-trichlorophenyl)[4-(isoxazol-3-yl-5-carboxylic acid ethyl ester)-1,3-thiazol-2-yl]amine;
or a solvate, hydrate or a pharmaceutically acceptable salt thereof.

* * * * *